US009234841B2

(12) United States Patent
Wang et al.

(10) Patent No.: US 9,234,841 B2
(45) Date of Patent: Jan. 12, 2016

(54) OPTICAL TIME REVERSAL BY ULTRASONIC ENCODING IN BIOLOGICAL TISSUE

(75) Inventors: Lihong Wang, St. Louis, MO (US); Xiao Xu, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 67 days.

(21) Appl. No.: 13/574,994

(22) PCT Filed: Jan. 24, 2011

(86) PCT No.: PCT/US2011/022253
§ 371 (c)(1),
(2), (4) Date: Aug. 14, 2012

(87) PCT Pub. No.: WO2011/091360
PCT Pub. Date: Jul. 28, 2011

(65) Prior Publication Data
US 2012/0307250 A1    Dec. 6, 2012

Related U.S. Application Data

(60) Provisional application No. 61/298,086, filed on Jan. 25, 2010.

(51) Int. Cl.
*G01B 11/02*    (2006.01)
*G01N 21/49*    (2006.01)
(Continued)

(52) U.S. Cl.
CPC ............ *G01N 21/49* (2013.01); *G01N 21/1717* (2013.01); *G01N 21/6456* (2013.01); *G01N 21/6458* (2013.01); *G01N 2021/1708* (2013.01); *G01N 2021/1785* (2013.01)

(58) Field of Classification Search
CPC ................................ G01B 11/00; G01N 21/49
USPC .......................................................... 356/502
See application file for complete search history.

(56) References Cited

U.S. PATENT DOCUMENTS 4,029,756 A * 6/1977 Gaafar ......................... 435/7.36
4,284,324 A    8/1981 Huignard et al.
(Continued)

FOREIGN PATENT DOCUMENTS

JP    2009-068977 A    4/2009
WO    2008/062354 A1    5/2008
WO    2011/091360 A2    7/2011

OTHER PUBLICATIONS

Notification of Transmittal of the International Search Report and the Written Opinion of the International Searching Authority, Sep. 22, 2011, from related application No. PCT/US2011/022253, 8 pgs.
(Continued)

*Primary Examiner* — Tarifur Chowdhury
*Assistant Examiner* — Omar Nixon
(74) *Attorney, Agent, or Firm* — Armstrong Teasdale LLP

(57) ABSTRACT

Generating an optical-phase conjugation of ultrasonically-modulated diffuse light emitted by a scattering medium includes illuminating the medium with a light beam from a coherent light source, modulating the diffuse light transmitted through the medium with an ultrasonic wave focused on a region of interest within the medium, and retro-reflectively illuminating the medium using a phase-conjugated copy of the diffuse light that was ultrasonically modulated.

20 Claims, 5 Drawing Sheets

(51) Int. Cl.
  *G01N 21/17*  (2006.01)
  *G01N 21/64*  (2006.01)

(56) References Cited

U.S. PATENT DOCUMENTS

| | | | |
|---|---|---|---|
| 4,546,771 | A | 10/1985 | Eggleton et al. |
| 4,921,333 | A | 5/1990 | Brody et al. |
| 5,329,817 | A | 7/1994 | Garlick et al. |
| 5,546,187 | A * | 8/1996 | Pepper et al. ............. 356/487 |
| 6,055,097 | A | 4/2000 | Lanni et al. |
| 6,590,830 | B1 | 7/2003 | Garlick et al. |
| 2005/0168749 | A1 * | 8/2005 | Ye et al. .................... 356/458 |
| 2006/0235299 | A1 | 10/2006 | Martinelli |
| 2007/0213590 | A1 | 9/2007 | Squicciarini |
| 2008/0037367 | A1 | 2/2008 | Gross et al. |
| 2009/0116518 | A1 | 5/2009 | Patel et al. |
| 2011/0071402 | A1 * | 3/2011 | Masumura .................... 600/476 |
| 2011/0122416 | A1 | 5/2011 | Yang et al. |
| 2012/0070817 | A1 | 3/2012 | Wang et al. |

OTHER PUBLICATIONS

Non-Final Office Action from related U.S. Appl. No. 13/143,832 dated Apr. 18, 2014, 14 pgs.

Xu et al., "Time Reversal Ultrasound Modulated Optical Tomography Using a BSO Phase Conjugate Mirror," poster presented at SPIE Conference 7177 on Jan. 26, 2009; 3 pgs.

* cited by examiner

US 9,234,841 B2

OPTICAL TIME REVERSAL BY ULTRASONIC ENCODING IN BIOLOGICAL TISSUE

CROSS REFERENCE TO RELATED APPLICATIONS

This application claims priority to PCT/US2011/022253 filed Jan. 24, 2011, which claims the benefit of U.S. Provisional Patent Application No. 61/298,086 filed Jan. 25, 2010, each of which is hereby incorporated by reference in its entirety.

STATEMENT REGARDING FEDERALLY SPONSORED RESEARCH & DEVELOPMENT

This invention was made with government support under grants R01 CA094267 and R01 CA106728, awarded by the U.S. National Institutes of Health. The government has certain rights in the invention.

BACKGROUND

Optical imaging through a highly scattering medium, such as biological tissue, has been stymied by the loss of optical focusing inside such a medium. Current optical imaging techniques, such as optical coherence tomography, image up to approximately one optical transport mean free path, such as about 1 millimeter (mm), into biological tissues. Other well-known techniques, such as confocal microscopy and multi-photon microscopy, have an even more restricted penetration path. Other imaging techniques, such as diffuse optical tomography or thermal wave microscopy, have a low depth to resolution ratio.

BRIEF DESCRIPTION

Embodiments described herein provide methods, systems, and apparatus for generating a time reversed reflection of diffuse light that emerges from a region of interest in a highly scattering medium. The scattering medium is illuminated with a coherent light source, and the diffuse light that emerges is modulated with a focused ultrasonic wave in the region of interest inside the scattering medium. The scattering medium is then retro-reflectively illuminated using a phase-conjugated copy of the modulated diffuse light wavefront. The phase-conjugated optical wave is focused back towards the ultrasonic focal zone, which enables light delivery to the selected region of interest, inside the highly scattering medium, that is defined by the ultrasonic focus. The embodiments described herein facilitate improving a spatial resolution of a variety of imaging modalities, as well as efficiency and accuracy of many clinical applications that involve non-invasive light delivery and manipulation to specific sites within a human or animal body.

BRIEF DESCRIPTION OF THE DRAWINGS

The embodiments described herein may be better understood by referring to the following description in conjunction with the accompanying drawings.

DETAILED DESCRIPTION

Figure 1:
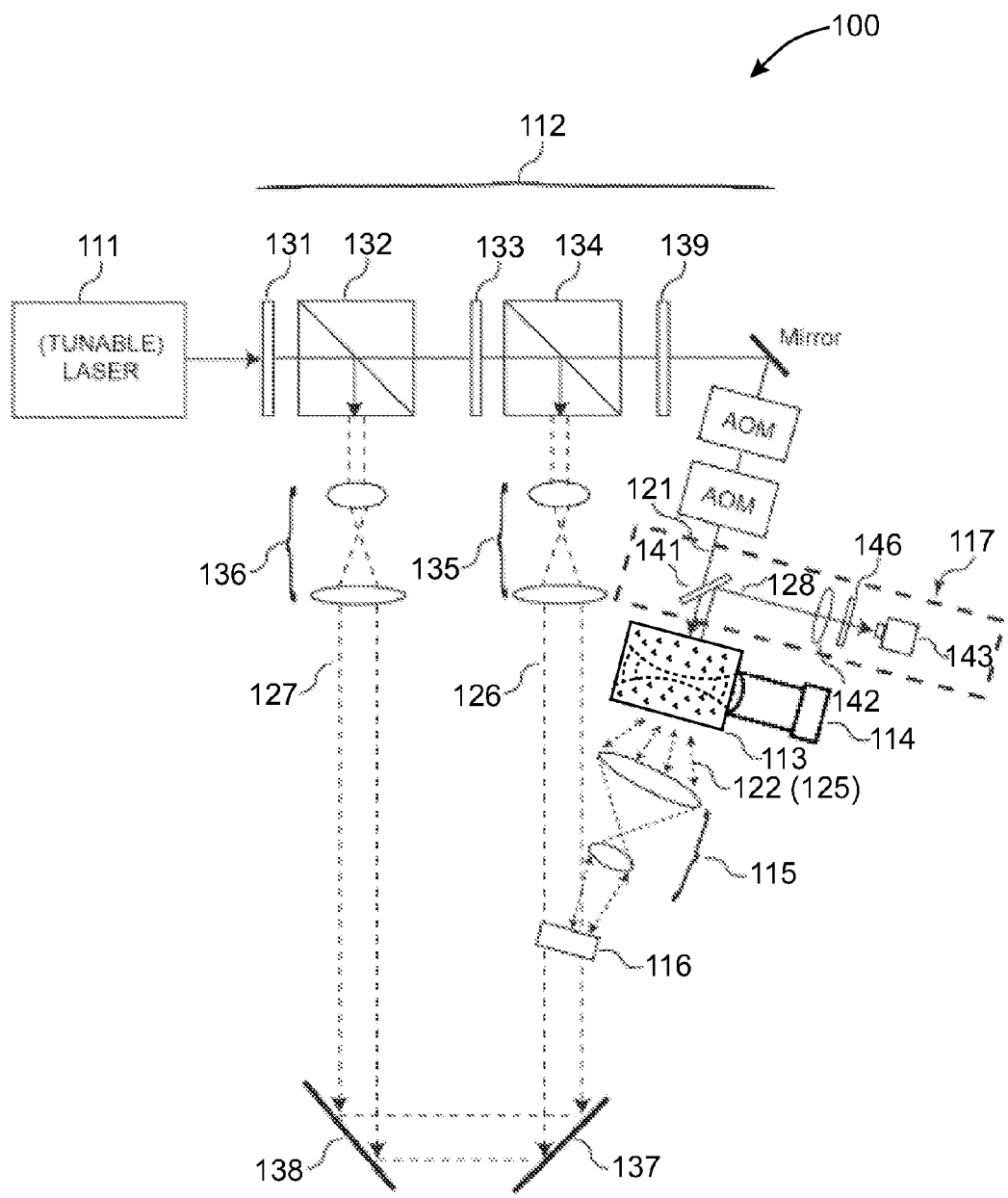
FIG. 1 is a diagram of an optical setup of a fluorescence imaging system based on optical time reversal by ultrasonic encoding.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. Terms defined herein have meanings as commonly understood by a person of ordinary skill in the arts relevant to the embodiments described herein. Terms such as "a," "an," and "the" are not intended to refer to only a singular entity, but include the general class of which a specific example may be used for the illustration. The terminology herein is used to describe specific embodiments of the present invention, but their usage does not limit the invention to the embodiments described herein, except as outlined in the claims.

To be consistent with the commonly used terminology, whenever possible, the terms used herein will follow the definitions recommended by the Optical Society of America (OCIS codes).

In some embodiments, the term "ultrasound modulated optical tomography" refers generally to a diffuse light imaging technology that detects diffuse light emanating from a turbid scattering medium, such as a biological tissue, that is modulated by ultrasonic wave focused in the region of interest inside the volume. Tomographic information of the optical properties of the medium with ultrasound resolution may be obtained by raster scanning the ultrasound beam through the medium.

In some embodiments, the terms "optical phase conjugation," "wavefront reversal," and "time-reversal reflection" refer generally to a process that precisely reverses the direction of propagation of each plane wave in an arbitrary light beam, thereby causing the return beam to exactly retrace the path of the incident beam.

In some embodiments, the term "photorefractive material" refers generally to a class of materials whose index of refraction changes when exposed to light because of electro-optic and photoconductive effects.

In some embodiments, the term "transducer array" refers generally to an array of ultrasonic transducers.

In some embodiments, the terms "focused ultrasonic detector," "focused ultrasonic transducer," and "focused piezoelectric transducer" refer generally to a curved ultrasonic transducer with a hemispherical surface or a planar ultrasonic transducer with an acoustic lens attached or an electrically focused ultrasonic array transducer.

In some embodiments, the terms "transducer array" and "phase array transducer" refer generally to an array of piezoelectric ultrasonic transducers.

Light focusing plays a central role in biomedical imaging, manipulation and therapy. In scattering media, direct light focusing generally becomes infeasible beyond one transport mean free path. At least some known previous methods used to overcome this diffusion limit lack a practical internal "guide star." The embodiments described herein provide a concept called time-reversed ultrasonically encoded (TRUE) optical focusing to deliver light into any dynamically defined location inside a scattering medium. First, diffused coherent light is encoded by a focused ultrasonic wave to provide a virtual internal guide star. Only the encoded light is time-reversed and transmitted back to the ultrasonic focus. The time-reversed ultrasonically encoded optical focus—defined by the ultrasonic wave—is unaffected by multiple scattering of light. Such focusing is particularly desirable in biological tissue, where ultrasonic scattering is approximately 1,000 times weaker than optical scattering. Various fields, including biomedical and colloidal optics, can benefit from optical focusing.

Manipulating light propagation has been the subject of intense research. As the only electromagnetic wave sensitive to molecular conformation, light is an essential tool for probing the structure and properties of matter and to monitor physical, chemical or biological processes. Light (rather than harmful X-rays) is an ideal non-ionizing radiation for imaging and treating biological tissues. Light is also a basic tool in communications and computing.

Of particular interest is the problem of focusing light into a scattering medium. High-resolution optical imaging relies on being able to precisely focus light into a medium at a desired depth. Photodynamic therapy and optogenetics require light to be delivered to specific regions of interest inside tissue. However, multiple scattering imposes a fundamental optical diffusion limit on direct light focusing in scattering media. Consequently, the imaging depth of known forms of focusing optical microscopy, such as confocal microscopy, is limited to less than one transport mean free path. A number of technologies have been developed to address this problem. For example, light can be focused through biological tissue by optical phase conjugation, or focused into a static scattering medium by iterative wavefront shaping, which maximizes the signal strength of a blurred yet visible implanted target. However, it is desirable to focus light into (instead of through) a scattering medium, to tolerate dynamic microstructures, and to rapidly adjust the focal position. These challenges have not been met by known research endeavors.

As described hereinbelow, embodiments of the present invention provide a method for generating a time-reversed reflection of the diffuse light that emerges from a region of interest in a highly scattering medium such as biological tissue. The method includes illuminating the scattering medium with a coherent light source and modulating the diffuse light with a focused ultrasonic wave in the region of interest inside the scattering medium. The method also includes retro-reflectively illuminating the scattering medium using the phase-conjugated copy of the modulated diffuse light wavefront. The phase-conjugated light converges to the ultrasound focal zone, which functions as a virtual aperture. This focused phase-conjugated light may be used to locally illuminate the region of interest to either improve the spatial resolution of a variety of optical imaging modalities or improve the accuracy and efficiency of non-invasive light delivery in many biological and clinical applications such as photodynamic therapy and opto-genetics.

Embodiments of the invention provide encoding of a diffuse light wave with localized ultrasound modulation inside a highly scattering medium. Optical phase conjugation of this ultrasound-modulated light generates a time-reversed wavefront that converges back to the ultrasound focus within the same scattering medium. In other words, embodiments of the invention provide a method to focus light into a scattering medium, which would otherwise diffuse light. Embodiments of this method improve spatial resolution for an array of optical imaging modalities. Moreover, embodiments of this method enable efficient and accurate non-invasive light delivery to selected sites inside a scattering medium for biological and/or clinical applications such as photodynamic therapy and/or opto-genetics.

Illumination of the tissue is provided by a long coherence length CW laser operating at a selected wavelength suitable for imaging biological tissue. The focused ultrasonic wave is sent by a single-element focused ultrasonic transducer, or by an array of ultrasonic transducers, that is capable of producing an ultrasonic wave localized within the targeted region. Optical phase conjugation (also referred to as time reversal) is realized by: (1) holographically recording the interference pattern between the signal light $\overset{\omega}{S}$ that is scattered from the tissue, and a reference light beam $\overset{\omega}{R}$ that is derived from the same laser source; and (2) subsequently reading the hologram using a second light beam $\overset{\omega}{R}{}^*$ that is the phase conjugate of the first reference beam $\overset{\omega}{R}$. As a result, the phase-conjugated wavefront of $\overset{\omega}{S}$ from diffraction of the hologram, as denoted by $\overset{\omega}{R}{}^*$, is produced. The reference light beam $\overset{\omega}{R}$ and its conjugate beam $\overset{\omega}{R}{}^*$ are derived from the same laser source that illuminates the tissue to produce the diffuse light $\overset{\omega}{S}$. An optical assembly, which generally consists of lenses, wave plates, and/or beam splitters, is used to derive $\overset{\omega}{R}$ and $\overset{\omega}{R}{}^*$, and to control the beam shape and intensity. The diffuse light $\overset{\omega}{S}$ is collected by an optical assembly, typically consisting of lenses, mirrors, and/or optical fiber bundles, and directed onto the phase conjugating device. The phase conjugating device, usually a photorefractive material of choice that operates at the laser wavelength, is used to record and read the hologram dynamically through the write-read cycles. In order to match the frequency of the ultrasound modulated component of the diffuse light $\overset{\omega}{S}$ and that of the reference light $\overset{\omega}{R}$, $\overset{\omega}{S}{}^*$, one acousto-optic modulator (AOM), or two in tandem, are used to frequency shift the laser beam before it is incident on the tissue, by the amount equal to the central frequency of the applied ultrasonic wave.

In addition, embodiments described herein may include one or more ultrasonic transducers or a combination thereof. The optical setup may include components to deliver light in free space or in optical fibers, to regulate the beam shapes, polarizations, and intensities, and to detect light intensities, such as mirrors, lenses, wave plates, polarizers, filters, isolators, shutters, photodiodes, and photomultipliers. The phase conjugating device may include an assembly of devices capable of dynamic holography such as photorefractive materials, CCD cameras, and spatial light modulators. The electronic system includes scanner drivers and controllers, an amplifier, a digitizer, a laser wavelength tuning electronic system, a computer, a processor, a display, a storage device, or any combination thereof. One or more components of the electronic system may be in communication remotely with the other components of the electronic system, the scanning apparatus, or both.

The optical time-reversal system described herein, which is integrated in a transmission mode fluorescence imaging system, is one of the possible embodiments, and may be used with medical and biological applications. However, the optical time-reversal system is not limited to such applications.

Applications of the embodiments described herein include, but are not limited to: (1) a variety of imaging modalities in a scattering medium, such as fluorescence imaging, ultrasound-modulated optical tomography, diffuse optical tomography, and photoacoustic tomography; and (2) many biological and clinical processes that use nonintrusive localized light delivery and manipulation inside the human and/or animal body, such as photodynamic therapy and opto-genetics.

Embodiments of the invention include any realization of an optical imaging device that uses a focused ultrasonic wave to modulate a temporally coherent light wave inside a highly scattering medium, and subsequently generates the time-reversed wavefront of the ultrasound-modulated light to back-illuminate the same scattering medium to excite fluorescence for imaging purposes. The following devices are capable of performing the methods described herein: (1) a transmission-mode fluorescence imaging system that collects back-scattered ultrasound-modulated light from an incident side and detects fluorescence light from the opposite side of the scattering medium; (2) a reflection-mode fluorescence imaging system that collects the forward-scattered ultrasound-modulated light and detects the fluorescence light from the opposite side of the scattering medium; and (3) a reflection-mode fluorescence imaging system that collects the back-scattered ultrasound-modulated light and detects the fluorescence light from the incident side of the scattering medium.

FIG. 1 is a diagram of an exemplary fluorescence imaging system 100 with optical time reversed excitation by ultrasonic encoding. A light beam 121 originates from a laser 111 through beam control 112, and is transmitted through first and second successively positioned polarizing beam splitters 132 and 134. The original laser beam is split by the first and second polarizing beam splitters 132 and 134 into first and second mutually conjugated reference light beams 126 and 127, respectively. Only one of the mutually conjugated reference light beams 126 and 127 is active at any time. The on-off states and the relative intensities of the light beams 121, 126, and 127 are controlled by first and second Pockels cells 131 and 133, each positioned in front of a respective beam splitter 132 and 134. The reference beams 126 and 127 are expanded and collimated by first and second collimating optics 135 and 136, respectively, each of which is positioned after respective beam splitters 132 and 134. First and second steering mirrors 137 and 138 are positioned after the collimating optics 135 and 136, respectively, and are adjusted such that the reference beams 126 and 127 precisely retrace the propagation profile of each other to constitute a mutually conjugated pair. The light beam 121 is transmitted through a half wave plate 139 to align the polarization of the light beam 121 with the polarization of the reference beam 126 and then through two acousto-optic modulators 141 and 142 in series, such that the optical frequency of the light beam 121 is shifted by the frequency difference $f_0$ of the driving frequencies of the two acousto-optic modulators 141 and 142 before illuminating a biological tissue 113.

Scattered light 122 emerging from the biological tissue 113 is modulated inside the biological tissue 113 by the focused ultrasound emanating from an ultrasound transducer 114 that is driven at the frequency $f_0$. In the spectral domain, the scattered light 122 is composed of a series of harmonics of the ultrasonic frequency $f_0$, with the first harmonic having the same frequency as the reference light 126 and 127, and the strength proportional to the modulation depth M, which is characteristic of the ultrasound light interaction inside the biological tissue 113 that may be mostly attributed to the interaction within the focal zone of the ultrasound transducer 114. Collimating optics 115, such as a pair of lenses, collect the scattered light 122 into a photorefractive crystal 116, such as $Bi_{12}SiO_{20}$ or BSO, where a dynamic hologram of the interference pattern between the scattered light 122 and the first reference beam 126 is recorded. A stable interference pattern that is typically recorded is between the first harmonic component of the scattered light 122 and the first reference light 126. The recording period, which is dependent on the $Bi_{12}SiO_{20}$ material properties and on the intensity of the two recording beams 122 and 126, is faster than the speckle decorrelation time caused by the natural motion of the target tissue 113.

After the hologram is recorded, the first Pockels cell 131 in front of the first polarizing beam splitter 132 is tuned such that the light beam 121 and the first reference beam 126 are turned off and the second reference beam 127 is turned on. The second reference beam 127 illuminates the photorefractive crystal 116, generating from its diffraction off the hologram the light beam 125, which is the phase conjugate of the first harmonic of the scattered light 122. The light beam 125 retraces the propagation paths of the scattered light 122 to illuminate on the back side of the biological tissue 113 and converges to the focal zone of the ultrasound transducer 114 from where the first harmonic component of the scattered light 122 originates. Consequently fluorescence light 128 is excited within the ultrasonic focal zone and emerges from the biological tissue 113. Although this embodiment detects fluorescent light from the front side of the tissue 113, in alternative embodiments, detection from other sides of the tissue 113 is also possible. The intensity of the fluorescence light 128 is detected by a signal detector 117 that includes a dichroic beam splitter 141 followed by a focusing lens 142 and an optical filter 146 positioned in front of a photodetector 143. This signal is then transferred to a computer for data analysis to recover the fluorescence image of the biological tissue 113 through raster or three-dimensional (3D) scan.

Figure 2:
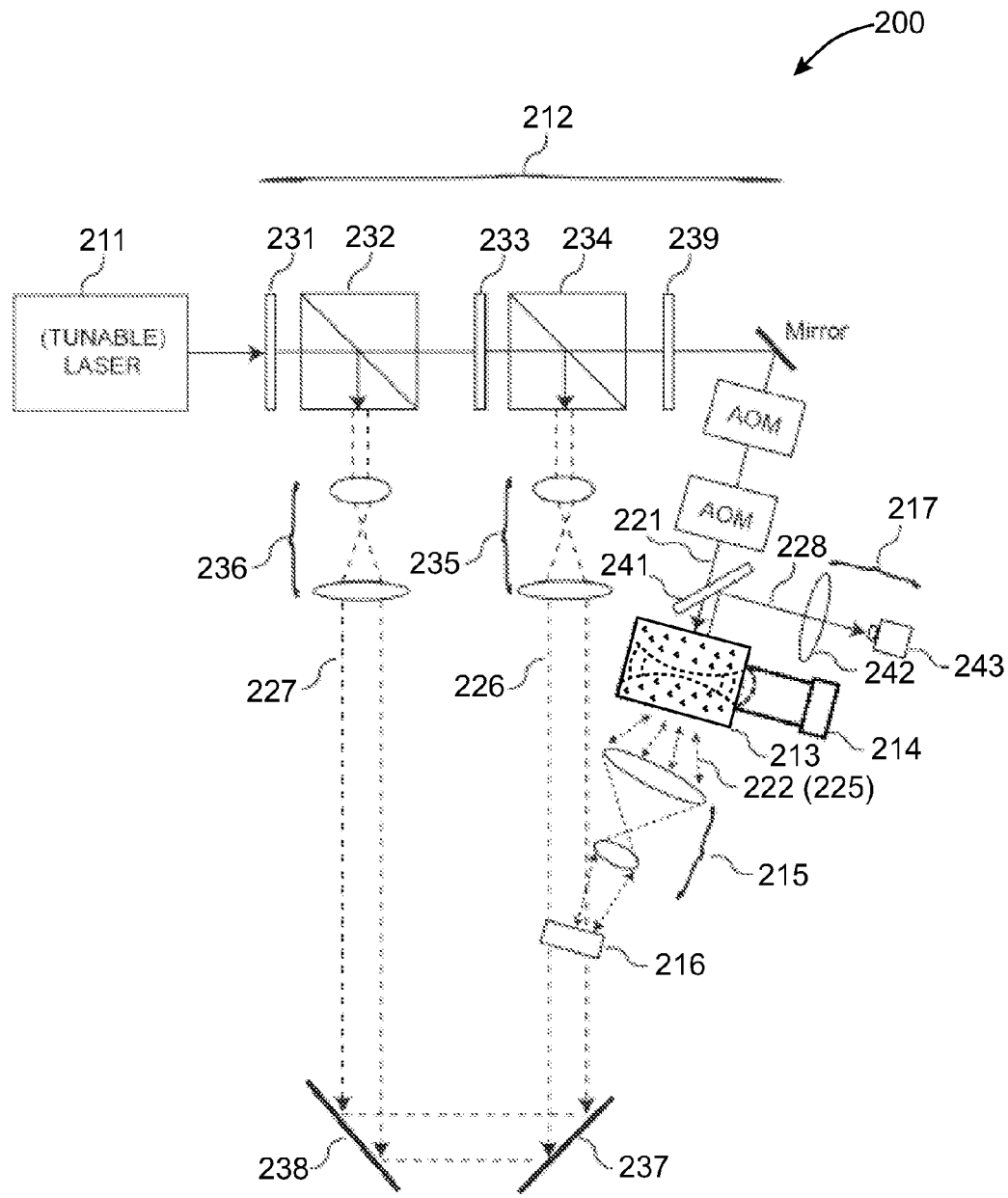
FIG. 2 is a diagram of an alternative embodiment of an ultrasound-modulated optical imaging system based on optical time reversal by ultrasonic encoding.

FIG. 2 is a diagram of an alternative embodiment of an ultrasound-modulated optical imaging system 200 based on optical time reversal by ultrasonic encoding in accordance with the imaging system shown in FIG. 1.

The ultrasound-modulated optical imaging system 200 is similar to the fluorescence imaging system 100 (shown in FIG. 1), except that the transducer array 214 is used to transmit a focused ultrasonic wave to modulate the diffuse light in the region of interest inside the biological tissue 213. The ultrasonic transducer array 214 is tuned so that the ultrasonic wave that modulates the diffuse light when the biological tissue 213 is illuminated by the time reversed light 225 has a tighter focus than the ultrasonic wave that modulates the light beam 221. Moreover, the signal detector 217 detects the ultrasound-modulated light 228 resulting from the diffusion of the time reversed light 225 through the biological tissue 213. The light 228 has a much higher modulation depth M' because most of the time reversed light 225 passes through the ultrasound focus. This renders the ultrasound-modulated optical imaging system 200 a higher signal-to-noise ratio than a conventional ultrasound-modulated optical imaging system.

Figure 3:
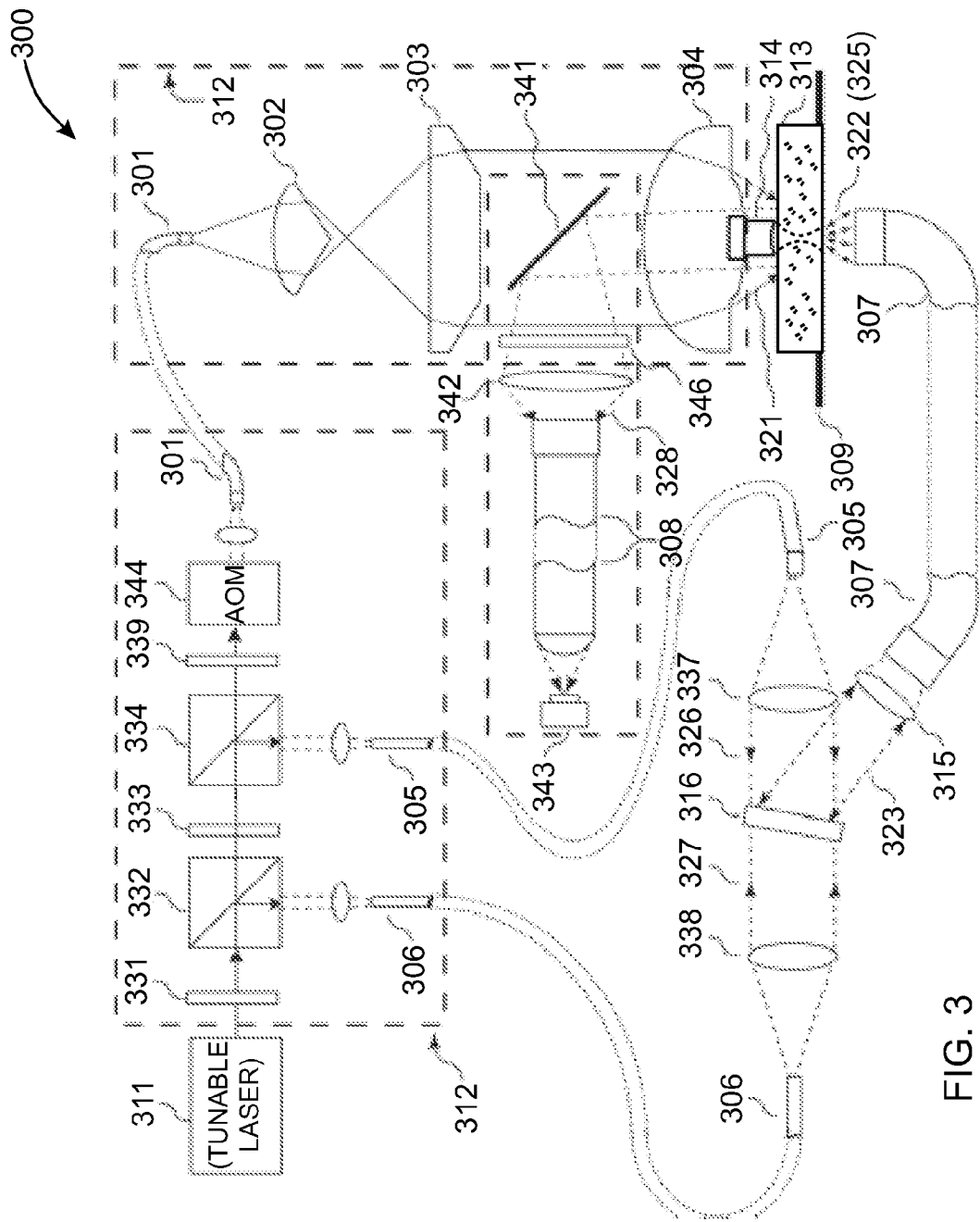
FIG. 3 is a diagram of another alternative embodiment of a transmission mode fluorescence microscope based on optical time reversal by ultrasonic encoding.

FIG. 3 is a diagram of another alternative embodiment of a transmission-mode fluorescence microscope 300 based on optical time reversal by ultrasonic encoding in accordance with the imaging system show in FIG. 1.

Coherent light out of a laser 311 is divided by two successive polarizing beam splitters 332 and 334 into three polarization maintaining optical fibers 301, 305, and 306. Two Pockels cells 331 and 333, each positioned in front of a respective beam splitter 332 and 334, control the intensity of the light that is coupled into the optical fibers 301, 305, and 306. A half wave plate 339 positioned after the second beam splitter 334 aligns the polarization of light coupled into the first optical fiber 301 to the polarization of light coupled into the second and third optical fibers 305 and 306. The light 321 is frequency shifted by an AOM 344 by an amount equivalent to the center frequency of an ultrasonic transducer 314, and is transmitted by the first optical fiber 301 through three aspheric lenses 302, 303, and 304, and is annularly focused into biological tissue 313 from its top. Scattered light 322 emerging from the bottom of the biological tissue 313 is delivered by an optical fiber bundle 307 and collimated by a lens 315 to a phase-conjugating device 316. After retro-reflection, phase conjugated light 325 from the phase-conjugating device 316 is delivered by the optical fiber bundle 307 to illuminate the biological tissue 313 from its bottom. Fluorescence light 328 emerging from the top side of the biological tissue 313, and excited by the phase conjugated light 325 in the region of interest inside the biological tissue 313, is transmitted through the third aspheric lens 304, reflected by a dichroic beam splitter 341, transmitted through an optical filter 346 and a focusing lens 342, and coupled into an optical fiber 308 before being detected by a photo detector 343. The intensity of the fluorescence light 328 is detected and transferred to a computer for signal analysis to recover an image of the biological tissue 313 from a raster scan or 3D scan.

The diffuse light inside the biological tissue 313 when it is illuminated by the light 321 is modulated by the focused ultrasonic wave sent from the focused ultrasound transducer 314. As a result, the phase conjugated light 325 retraces the propagation paths of the diffuse photons of the scattered light 322 that traverses the ultrasonic focal zone. The two mutually conjugated reference light beams necessary for the phase conjugation are delivered by the second and third optical fibers 305 and 306. The reference light 326 delivered by the second optical fiber 305 is collimated by a first lens 337, and the reference light 327 delivered by the third optical fiber 306 is collimated by a second lens 338. The alignment of the reference light beams 326 and 327 is such that they constitute a mutually conjugated pair. The interference pattern between the reference light beam 326 and the scattered light 323 out of the optical fiber bundle 307 is holographically recorded into the photorefractive material 316, such as $Bi_{12}SiO_{20}$ or BSO. After the hologram is engraved, the two Pockels cells 331 and 333 are tuned to turn off the light beam 321 and the reference beam 326, and turn on the reference beam 327 to read out the hologram, which generates the phase conjugated light 325. A loading stage 309 may be raster scanned so that the entire region of interest of the biological tissue 313 may be imaged.

Figure 4:
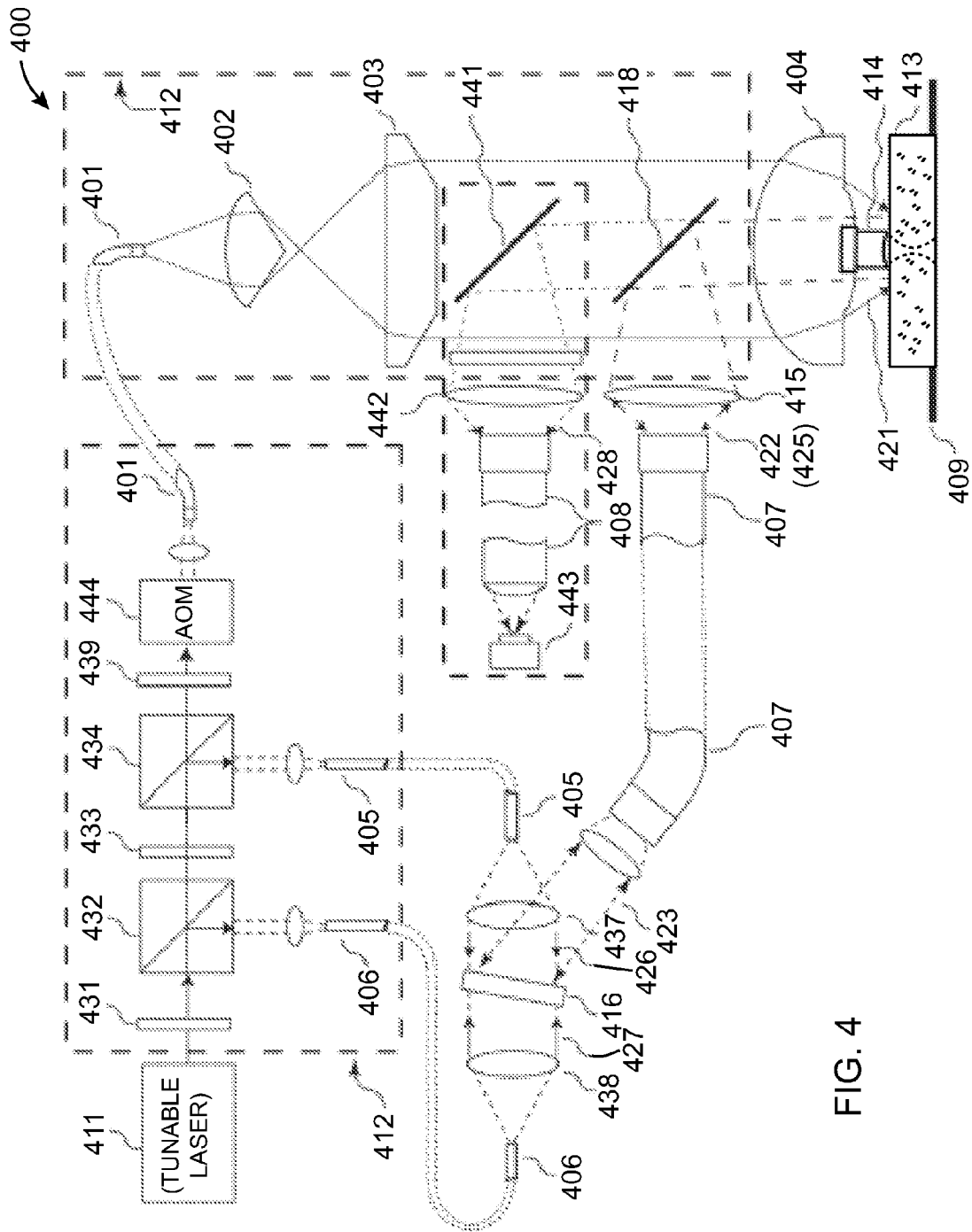
FIG. 4 is a diagram of another alternative embodiment of a reflection-mode fluorescence microscope based on optical time reversal by ultrasonic encoding.

FIG. 4 is a diagram of another alternative embodiment of a reflection-mode fluorescence microscope 400 based on optical time reversal by ultrasonic encoding in accordance with the imaging system shown in FIG. 1.

The reflection mode fluorescence microscope 400 is similar to the transmission-mode fluorescence microscope shown in FIG. 3, except that back-scattered light 422 is collected from the incident side of a light beam 421 where it is reflected by a dichroic beam splitter 418 and coupled by a focusing lens 415 into one or more fiber bundles 407.

Figure 5:
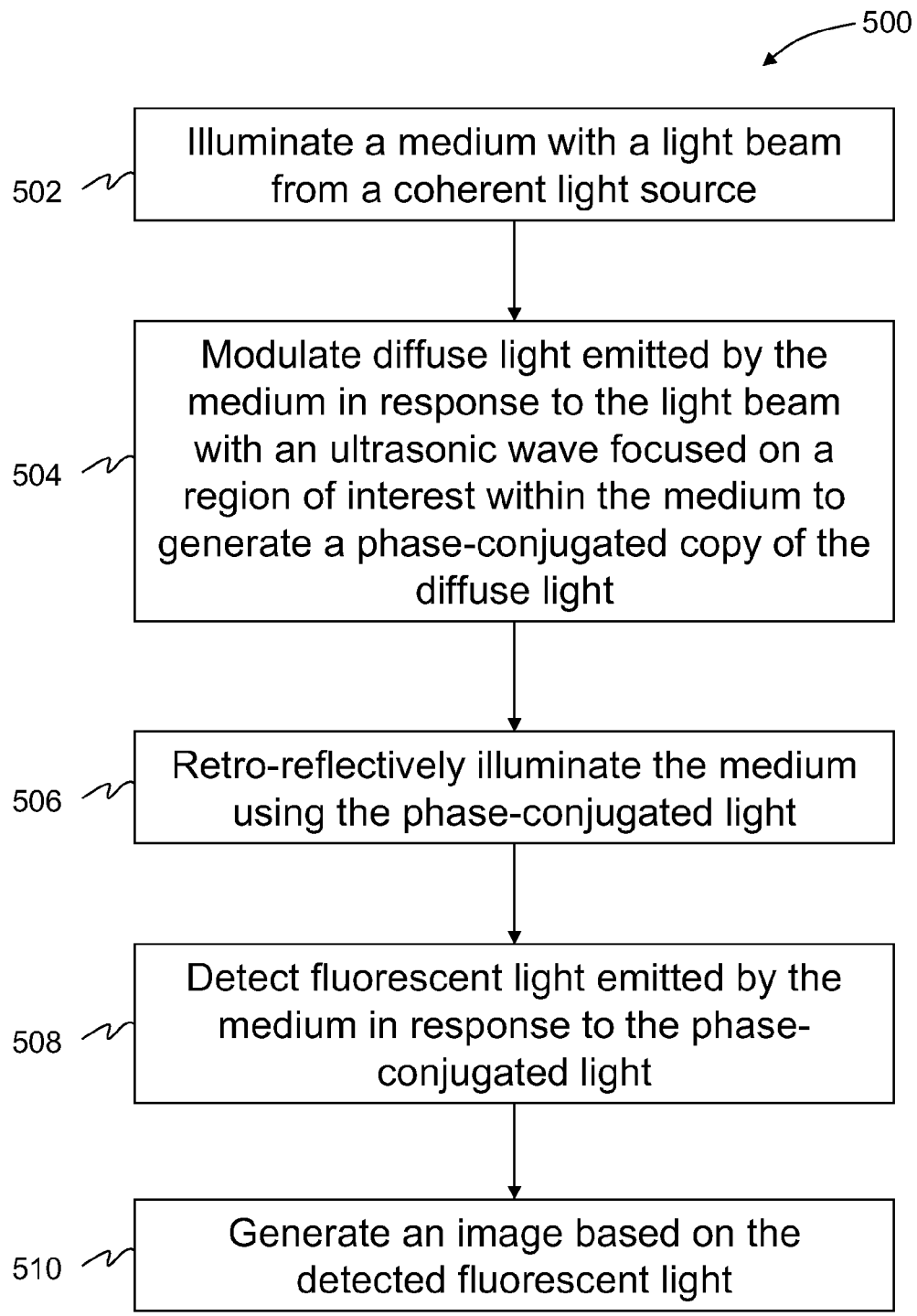
FIG. 5 is a flowchart illustrating an exemplary method of fluorescence imaging.

FIG. 5 is a flowchart 500 that illustrates an exemplary method for generating an optical-phase conjugation of diffuse light emitted by a highly scattering medium, such as biological tissue 113 (shown in FIG. 1). One or more of the operations described in FIG. 5 may be executed by a computer or processor. Moreover, the flowchart 500 shown in FIG. 5 is an example of an algorithm that may be executed by a computer or processor for generating an optical-phase conjugation of diffuse light emitted by a highly scattering medium, such as biological tissue 113. Referring to FIG. 1, and in an exemplary embodiment, a medium, such as tissue 113, is illuminated 502 using a light beam 121 that is emitted by a coherent light source, such as continuous wave laser 111. For example, the light beam 121 is split by polarizing beam splitters 132 and 134 into two mutually conjugated reference light beams 126 and 127. The reference light beams 126 and 127 are expanded and collimated by collimating optics 135 and 136, respectively. Moreover, the light beam 121 is transmitted through half wave plate 139 to align the polarization of the light beam 121 with the polarization of the first reference light beam 126. The light beam 121 is also transmitted through two acousto-optic modulators 141 and 142 to shift the optical frequency of the light beam 121, and the light beam 121 illuminates the tissue 113.

Moreover, in an exemplary embodiment, diffuse, or scattered, light 122 emitted by the tissue 113 is modulated 504 using a focused ultrasonic wave emitted by an ultrasound transducer 114 inside the tissue 113. Collimating optics 115 collect the diffuse light into a phase-conjugating device, such as photorefractive crystal 116. A dynamic hologram of an interference pattern between the diffuse light 122 and the first reference beam 126 is recorded, such as holographically recorded, by the photorefractive crystal 116.

In an exemplary embodiment, and after the hologram is recorded, the first Pockels cell 131 is tuned to deactivate the light beam 121 and the first reference beam 126, and to activate the second reference beam 127. The second reference beam 127 illuminates the photorefractive crystal 116 such that the photorefractive crystal 116 generates from its diffraction off the hologram a light beam 125 that is the phase conjugate of the first harmonic of the diffuse light 122. The light beam 125 retraces the propagation paths of the diffuse light 122 to retro-reflectively illuminate 506 the back side of the tissue 113 and converges to the focal zone of the ultrasound transducer 114. In response to the illumination from the back side of the tissue 113 by light beam 125, the tissue 113 emits fluorescence light 128 that is detected 508 by a signal detector 117. The signal detector 117 transmits a signal representative of the fluorescence light 128 to a computer, which generates 510 an image of an area of interest within the tissue 113 based on the detected fluorescent light 128.

TRUE optical focusing has been validated with imaging experiments. In one experiment, an imaging sample was a 10-mm-thick scattering slab, made from a mixture of porcine gelatine, distilled water and 0.25% Intralipid, resulting in $L_s\approx0.4$ mm, g≈0.9 and an absorption length $L_a\approx79$ mm. The light beam initially had a diameter of 2 mm on the incident plane of the sample and diffused to approximately 4 mm (FWHM) in the middle plane, which contained three objects with different compositions: two dyed with black ink, resulting in an optical absorption coefficient $\mu_a\approx0.8$ mm$^{-1}$, and one having 1% concentration Intralipid, resulting in $L_s\approx40$ 0.1 mm. When the sample was laterally scanned along the x-axis, four one-dimensional images were acquired. The first two were acquired without either AOM tuning or ultrasonic modulation. To form the first image (a "DC" image), S($f_s$) was detected by a photodiode at the BSO position. To form the second image (a "TRDC" image), S*($f_s$) was transmitted back through the sample and detected by a first photodiode. To form the third image (a "UOT" image based on conventional ultrasound-modulated optical tomography (UOT) 49 15,16), S($f_+$) was spectrally filtered by the BSO and then detected by a second photodiode. To form the fourth image (a "TRUE" image), S*($f_+$) was transmitted back through the sample and detected by the first photodiode.

The salient differences in the apparent image resolution and contrast among the four imaging methods stem from the distinct inherent imaging mechanisms. The DC and TRDC imaging methods, suffering from optical diffusion, lacked the spatial resolution to resolve the three objects. The optical diffusion, approximated as a Gaussian profile, was convolved with the object profile to fit the experimental data. The full-widths at half-maxima (FWHMs) of the Gaussian profiles, defined as the image resolutions, were 3.4 mm for DC imaging and 3.2 mm for TRDC imaging. In contrast, the UOT and TRUE imaging methods, based on imaging signals emanating from the internal virtual sources, both adequately depicted the profiles of the objects. The ultrasonic focus, approximated as a Gaussian profile, was convolved with the object profile to fit the data. The resolutions were 0.89 mm and 0.63 mm for UOT and TRUE imaging, respectively.

A square law exists if $S^*(f_+)$ indeed converges to the ultrasonic focus: the TRUE signal is proportional to the square of the UOT signal. On the one hand, the optical field for the UOT image is given by $S(x, f_+)|_{BSO} \propto C(x) \cdot S_{in}(f_s)$, where $C(x)$ is a virtual source term and $S_{in}(f_s)$ is the incident optical field. On the other hand, for the TRUE image, $S^*(x, f_+)|_{BSO} \propto S(x, f_+)|_{BSO}$. As $S^*(f_+)$ inversely traverses the sample, the virtual source term in its conjugated form $C^*(x)$ operates on $S^*(x, f_+)|_{BSO}$. As a result, the optical field detected by the first photodiode (PD1) is $S^*(x, f_s)|_{PD1} \propto C^*(x) \cdot S^*(x, f_+)|_{BSO} \propto |C(x)|^2 \cdot S_{in}(f_s)$. Therefore, the detected light intensities in UOT and TRUE imaging are related by $|S^*(x, f_s)|_{PD1}|^2 \propto |S(x, f_+)|_{BSO}|^4$. This prediction was verified by the normalized amplitudes of the UOT and TRUE images. Furthermore, if the pointspread functions in UOT and TRUE imaging follow Gaussian profiles, their widths—defining the spatial resolutions—have a $\sqrt{2}:1$ ratio. This second prediction agrees with the ratio of 1.4 between the image resolutions of UOT (0.89 mm) and TRUE (0.63 mm) imaging. In addition, the resolution of UOT is in agreement with the ultrasonic focal diameter of 0.87 mm.

Accordingly, focusing into a scattering medium is much more valuable than focusing through it. In fact, the former can be reduced to the latter by moving the focal position. Focusing through a medium is used to image a target outside a scattering medium, which can be either viewed directly from the target side or scanned by a collimated laser beam. Focusing into the medium must be used to image or treat a target embedded inside a scattering medium. For example, when a tumor inside biological tissue is optically imaged or treated, light must be focused to the tumor.

Moreover, focusing light into a scattering medium dynamically, with the desired speed and localization, can profoundly benefit studies involving photophysical, photochemical and photobiological processes. This work has demonstrated the feasibility of TRUE optical focusing by combining two key mechanisms—localized ultrasonic encoding of the diffused light and selective time reversal of the encoded light—to suppress the scattering effect. The focal spot size can be flexibly scaled with the ultrasonic frequency, and the experimental system can be adapted for reflection or other configurations according to the application. Alternative embodiments, can include faster photorefractive materials, time-reversal techniques with energy gains greater than unity, and more efficient time-reversal configurations. TRUE optical focusing—effectively bringing order to the chaotic scattering process—has potential in imaging technologies (such as fluorescence microscopy, diffuse optical tomography and photoacoustic tomography), manipulation technologies (such as optical tweezers and optogenetics), and therapeutic technologies (such as photodynamic and photothermal therapies).

Exemplary embodiments of methods, systems, and apparatus for use in optical time reversal by ultrasonic encoding in biological tissue are described above in detail. The methods, systems, and apparatus are not limited to the specific embodiments described herein but, rather, operations of the methods and/or components of the systems and/or apparatus may be utilized independently and separately from other operations and/or components described herein. Further, the described operations and/or components may also be defined in, or used in combination with, other systems, methods, and/or apparatus, and are not limited to practice with only the systems, methods, and apparatus described herein.

A computer or processor, such as those described herein, includes at least one processor or processing unit and a system memory. The computer or processor typically has at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Although the present invention is described in connection with an exemplary imaging system environment, embodiments of the invention are operational with numerous other general purpose or special purpose imaging system environments or configurations. The imaging system environment is not intended to suggest any limitation as to the scope of use or functionality of any aspect of the invention. Moreover, the imaging system environment should not be interpreted as having any dependency or requirement relating to any one or combination of components illustrated in the exemplary operating environment. Examples of well known imaging systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program components or modules, executed by one or more computers or other devices. Aspects of the invention may be implemented with any number and organization of components or modules. For example, aspects of the invention are not limited to the specific computer-executable instructions or the specific components or modules illustrated in the figures and described herein. Alternative embodiments of the invention may include different computer-executable instructions or components having more or less functionality than illustrated and described herein. A software module or program module may reside in random access memory (RAM), flash memory, read-only memory (ROM), erasable programmable read-only memory (EPROM), electrically erasable programmable read-only memory (EEPROM), registers, hard disk memory, a removable disk, a CD-ROM, or any other form of computer-readable storage medium known in the art.

The order of execution or performance of the operations in the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

It will be understood by those of skill in the art that information and signals may be represented using any of a variety of different technologies and techniques. For example, data, instructions, commands, information, signals, bits, symbols, and/or chips may be represented by voltages, currents, electromagnetic waves, magnetic fields or particles, optical fields or particles, or any combination thereof. Similarly, the various illustrative logical blocks, modules, circuits, and algorithm operations described herein may be implemented as electronic hardware, computer software, or a combination of both, depending on the application and the functionality. Moreover, the various logical blocks, modules, and circuits described herein may be implemented or performed with a general purpose computer, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Exemplary general purpose processors include, but are not limited to only including, microprocessors, conventional processors, controllers, microcontrollers, state machines, or a combination of computing devices.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for generating an optical-phase conjugation of diffuse light emitted by a scattering medium comprising:
    illuminating the medium with a light beam from a coherent light source;
    ultrasonically modulating the diffuse light transmitted through the medium with an ultrasonic wave focused on a region of interest within the medium; and
    retro-reflectively illuminating the medium using a phase-conjugated copy of the diffuse light that was ultrasonically modulated.

2. A method in accordance with claim 1, wherein the coherent light source comprises a continuous-wave laser.

3. A method in accordance with claim 1, further comprising transmitting the ultrasonic wave to the medium using at least one ultrasonic transducer.

4. A method in accordance with claim 1, further comprising holographically recording an interference pattern between the diffuse light emitted by the medium and a first reference light beam.

5. A method in accordance with claim 4, further comprising reading the hologram using a second reference light beam comprising a phase conjugate of the first reference light beam.

6. A method in accordance with claim 1, further comprising collecting the diffuse light using an optical assembly.

7. A method in accordance with claim 1, further comprising using a modulator to frequency shift the light beam from the light source by an amount equal to a central frequency of the ultrasonic wave.

8. An imaging system comprising:
    a continuous wave laser to emit a light beam and to illuminate a scattering medium such that diffuse light is emitted by the medium in response to the light beam;
    an ultrasonic transducer to modulate the diffuse light transmitted through the medium with an ultrasonic wave focused on a region of interest within the medium;
    a photorefractive device to create a phase-conjugated copy of the ultrasonically-modulated diffuse light and to illuminate the medium using the phase-conjugated light that converges to a focal zone of the ultrasonic wave; and
    a computer to control emission of the light beam by the laser.

9. An imaging system in accordance with claim 8, wherein the ultrasonic transducer comprises an array of ultrasonic transducers.

10. An imaging system in accordance with claim 8, wherein the photorefractive device records an interference pattern between the ultrasonically-modulated diffuse light emitted by the medium and a first reference light beam.

11. An imaging system in accordance with claim 10, wherein the photorefractive device further reads the hologram using a second reference light beam that is a phase conjugate of the first reference light beam.

12. An imaging system in accordance with claim 8, further comprising an optical assembly to collect the diffuse light.

13. An imaging system in accordance with claim 8, further comprising a modulator to frequency shift the light beam from the laser by an amount equal to a central frequency of the ultrasonic wave.

14. An imaging system in accordance with claim 8, wherein the imaging system comprises one of a transmission-mode fluorescence imaging system and a reflection-mode fluorescence imaging system.

15. An apparatus for use with an imaging system, the apparatus comprising:
    a continuous wave laser to emit a light beam and to illuminate a scattering medium such that diffuse light is emitted by the medium in response to the light beam;
    an ultrasonic transducer to modulate the diffuse light transmitted through the medium with an ultrasonic wave focused on a region of interest within the medium; and
    a photorefractive device to create a phase-conjugated copy of the ultrasonically-modulated diffuse light and to illuminate the medium using the phase-conjugated light that converges to a focal zone of the ultrasonic wave.

16. An apparatus in accordance with claim 15, wherein the photorefractive device records an interference pattern between the ultrasonically-modulated diffuse light emitted by the medium and a first reference light beam.

17. An apparatus in accordance with claim 16, wherein the photorefractive device further reads the hologram using a second reference light beam that is a phase conjugate of the first reference light beam.

18. An apparatus in accordance with claim 15, further comprising an optical assembly to collect the diffuse light.

19. An apparatus in accordance with claim 15, further comprising a modulator to frequency shift the light beam from the laser by an amount equal to a central frequency of the ultrasonic wave.

20. An apparatus in accordance with claim 15, wherein the apparatus comprises one of a transmission-mode fluorescence microscope and a reflection-mode fluorescence microscope.

* * * * *